(12) United States Patent
Zhao et al.

(10) Patent No.: US 12,024,734 B2
(45) Date of Patent: Jul. 2, 2024

(54) METHOD FOR TWO-PHASE PARTITIONING PRODUCTION OF MEDIUM-CHAIN FATTY ACID (MCFA) BY DRY ANAEROBIC DIGESTION

(71) Applicant: Institute of Environment and Sustainable Development in Agriculture, CAAS, Beijing (CN)

(72) Inventors: Lixin Zhao, Beijing (CN); Yi Liang, Beijing (CN); Jiadong Yu, Beijing (CN); Zonglu Yao, Beijing (CN); Juan Luo, Beijing (CN)

(73) Assignee: Institute of Environment and Sustainable Development in Agriculture, CAAS, Beijing (CN)

( * ) Notice: Subject to any disclaimer, the term of this patent is extended or adjusted under 35 U.S.C. 154(b) by 0 days.

(21) Appl. No.: 18/491,592

(22) Filed: Oct. 20, 2023

(65) Prior Publication Data

US 2024/0132924 A1     Apr. 25, 2024

(30) Foreign Application Priority Data

Oct. 21, 2022 (CN) .......................... 202211289922.X

(51) Int. Cl.
  *C12P 7/40* (2006.01)
  *C12P 7/6409* (2022.01)
  *C12R 1/145* (2006.01)
  *C12R 1/25* (2006.01)

(52) U.S. Cl.
  CPC ...... *C12P 7/6409* (2013.01); *C12R 2001/145* (2021.05); *C12R 2001/25* (2021.05)

(58) Field of Classification Search
  CPC .. C12P 7/6409; C12P 7/40; C12P 7/08; C12P 7/10
  See application file for complete search history.

(56) References Cited

FOREIGN PATENT DOCUMENTS

CN         112063661 A      12/2020

OTHER PUBLICATIONS

Yu et al., Influence factors of batch dry anaerobic digestion for corn stalks-cow dung mixture, Transactions of the Chinese Society of Agricultural Engineering, 2018, 34(15): 215-221.
Shen Qilong, General Theory of Soil and Fertilizer, Higher Education Press, 2021, ISBN 978-7-04-032461-7, 7 pages.

*Primary Examiner* — Tekchand Saidha
(74) *Attorney, Agent, or Firm* — Bookoff McAndrews, PLLC

(57) ABSTRACT

The present disclosure provides a method for two-phase partitioning production of a medium-chain fatty acid (MCFA) by dry anaerobic digestion. In the present disclosure, due to a slow heat transfer of the dry anaerobic digestion, a same dry anaerobic digestion device is naturally divided into two phases, and the MCFA is synthesized while producing electron acceptors and electron donors in the same dry anaerobic digestion device. Meanwhile, the dry anaerobic digestion device is provided with a high-efficiency decomposing microbial inoculant on an upper part and inoculated with sludge having a carbon chain extension function on a lower part. In this way, a material residence time is regulated, and cycles of hydrolytic acidification and carbon chain extension are shortened, thereby achieving the high-value conversion of agricultural waste while increasing a conversion rate of organic acids in the dry anaerobic digestion.

9 Claims, 2 Drawing Sheets

METHOD FOR TWO-PHASE PARTITIONING PRODUCTION OF MEDIUM-CHAIN FATTY ACID (MCFA) BY DRY ANAEROBIC DIGESTION

CROSS REFERENCE TO RELATED APPLICATION

This patent application claims the benefit and priority of Chinese Patent Application No. 202211289922.X, filed with the China National Intellectual Property Administration on Oct. 21, 2022, the disclosure of which is incorporated by reference herein in its entirety as part of the present application.

TECHNICAL FIELD

The present disclosure belongs to the technical field of resource utilization of agricultural waste, and in particular relates to a method for two-phase partitioning production of a medium-chain fatty acid (MCFA) by dry anaerobic digestion.

BACKGROUND

Cellulosic biomass such as straw is rich in carbon sources and is an ideal raw material for the production of short-chain fatty acids (SCFAs). The straw is generally co-fermented with protein-rich livestock and poultry manure such as cow manure and pig manure to balance nutrients in a resulting fermentation system. However, since SCFAs are easily soluble in water, it is difficult to recover the SCFAs from a fermentation broth. In contrast, medium-chain fatty acids (MCFAs) have the advantages of strong hydrophobicity and high added value, and are easier to extract from the fermentation broth; moreover, the MCFAs can be used as precursors in the production of drugs, food additives, lubricants, and solvents.

Carbon chain extension, as an important way to synthesize MCFAs, can convert SCFAs such as acetic acid and butyric acid, which are intermediate products of anaerobic digestion, into the MCFAs. This technology can not only realize the recycling of agricultural waste, but also produce MCFAs with a high added value, and save more cost than the traditional chemical method for synthesizing the MCFAs.

At present, the synthesis of MCFAs by anaerobic digestion mainly includes single-phase synthesis and two-phase synthesis. The single-phase synthesis accomplishes all reaction stages under the same ambient conditions. However, this process reduces a conversion rate of the MCFAs due to spontaneous generation of methane during production of the SCFAs by hydrolytic acidification. The two-phase synthesis is to separate the production of the SCFAs by hydrolytic acidification and the synthesis of the MCFAs by carbon chain extension, and it is difficult to match two-phase partitioning in this process.

Therefore, it needs further in-depth exploration to complete anaerobic digestion in an integrated anaerobic digestion device, to achieve production of the SCFAs by hydrolytic acidification and the carbon chain extension while improving conversion rate and efficiency of the MCFAs.

SUMMARY

In view of this, an objective of the present disclosure is to provide a method for two-phase partitioning production of a medium-chain fatty acid (MCFA) by dry anaerobic digestion. The present disclosure realizes the two-phase partitioning production of an MCFA with agricultural waste by integrated dry anaerobic digestion, and can improve a conversion rate of the MCFA.

The present disclosure provides a method for two-phase partitioning production of an MCFA by dry anaerobic digestion, including the following steps:

1) mixing straw, livestock and poultry manure, and a composite microbial inoculant to obtain a fermentation material; where the composite microbial inoculant includes *Lactobacillus plantarum* and *Clostridium*;

2) inoculating sludge at a bottom of a dry anaerobic digestion device, filling an upper part of the sludge with the fermentation material, and conducting first dry anaerobic digestion for 3 d to 7 d; where the sludge is acclimated by an acid;

3) conducting second dry anaerobic digestion by means of continuous feeding and discharging after the first dry anaerobic digestion is completed; where a material residence time and a material feeding-discharging frequency of the second dry anaerobic digestion are determined according to an average pH value and an average redox potential of a resulting intermediate material in a top ¼ to ⅓ area of the dry anaerobic digestion device after the first dry anaerobic digestion is completed;

when the intermediate material has an average pH value of less than 5.5 and an average redox potential of less than −350 mV, the second dry anaerobic digestion is conducted with a material residence time of 7 d to 15 d and a material feeding-discharging frequency of 48 h/time to 72 h/time;

when the intermediate material has an average pH of 5.5 to 6.5 and/or an average redox potential of −350 mV to −150 mV, the second dry anaerobic digestion is conducted with a material residence time of 5 d to 7 d and a material feeding-discharging frequency of 12 h/time to 24 h/time; and when the intermediate material has an average pH value of more than 6.5 and an average redox potential of more than −150 mV, the second dry anaerobic digestion is conducted with a material residence time of 3 d to 5 d and a material feeding-discharging frequency of 6 h/time to 12 h/time; and 4) subjecting a fermentation product obtained in the second dry anaerobic digestion to solid-liquid separation, and collecting a liquid component having the MCFA.

Preferably, the straw includes yellow corn silage straw; and the livestock and poultry manure includes cow manure.

Preferably, the straw and the livestock and poultry manure are at a mass ratio of 6:4 to 7:3; and the composite microbial inoculant accounts for 10% to 20% of a total mass of the straw and the livestock and poultry manure.

Preferably, the *Lactobacillus plantarum* and the *Clostridium* independently have an effective viable count of 0.1 billion cfu/g to 0.2 billion cfu/g; the *Lactobacillus plantarum* and the *Clostridium* are at an effective viable count ratio of 1:1; the *Lactobacillus plantarum* has a deposit number of CICC 21790; and the *Clostridium* has a deposit number of CICC 24702.

Preferably, the first dry anaerobic digestion and the second dry anaerobic digestion independently are conducted at 35° C. to 45° C.

Preferably, second dry anaerobic digestion is conducted at a pH value of 5.5 to 6.

Preferably, when a liquid produced in the upper ¼ to ⅓ area of the dry anaerobic digestion device flows to the lower ¼ to ⅓ area at a liquid decline rate of not more than 1.0 g/L to 1.5 g/L or the lower ¼ to ⅓ area of the dry anaerobic digestion device has a material porosity of not more than 25% to 30%, the material residence time is reduced to 9 d.

Preferably, the method further includes the following step after the liquid component having the MCFA is collected: extracting the MCFA in the liquid component.

Preferably, the method further includes the following step after the MCFA in the liquid component is extracted: refluxing a residual liquid obtained by the extraction to the dry anaerobic digestion device when lactic acid and acetic acid in the dry anaerobic digestion device have a total concentration of not more than 8 g/L to 10 g/L.

Preferably, the residual liquid obtained by the extraction has a reflux volume accounting for 10% to 20% of a feed amount by mass.

The present disclosure provides a method for two-phase partitioning production of an MCFA by dry anaerobic digestion. In the present disclosure, agricultural waste is fermented by using a composite microbial inoculant including *Lactobacillus plantarum* and *Clostridium*, which can efficiently hydrolyze and produce an SCFA. By adjusting a material ratio, a feeding method, and a material residence time, a material porosity, a production rate of the SCFA, a liquid decline rate, and the material porosity can be adjusted. A two-phase partitioning process is established, where a top ¼ to ⅓ area of the dry anaerobic digestion device can continue to produce the SCFA, forming a hydrolytic acidification area to produce the SCFA; a middle ¼ to ⅓ area is used as a transition area; and a bottom ¼ to ⅓ area continues to synthesize the MCFA, forming an MCFA synthesis area by carbon chain extension. In the dry anaerobic digestion device, the SCFA produced in the upper ¼ to ⅓ area flows with a resulting liquid to the lower ¼ to ⅓ area, such that the lower ¼ to ⅓ area has a reduced pH value. The reduced pH value is just suitable for the synthesis of MCFA by carbon chain extension bacteria, and it is easy to conduct the carbon chain extension; moreover, the MCFA is more efficiently synthesized under an action of the inoculated granular sludge with a carbon chain extension function. The method is based on the established integrated dry anaerobic digestion of two-phase partitioning process, and realizes self-regulation of the pH value of the lower ¼ to ⅓ area of a resulting fermentation system.

Compared with the existing single-phase synthesis, the present disclosure improves a production rate of the MCFA, and hardly produces methane; compared with the existing integrated two-phase synthesis, the present disclosure avoids the steps of phase separation and SCFA extraction and separation, and saves a cost in preparing the MCFA. Due to a slow heat transfer of the dry anaerobic digestion, a same dry anaerobic digestion device is naturally divided into two phases, and the MCFA is synthesized while producing electron acceptors and electron donors in the same dry anaerobic digestion device. Meanwhile, the dry anaerobic digestion device is provided with a high-efficiency decomposing microbial inoculant on an upper part and inoculated with granular sludge having a carbon chain extension function on a lower part. In this way, a material residence time is regulated, and cycles of hydrolytic acidification and carbon chain extension are shortened, thereby achieving the high-value conversion of agricultural waste while increasing a conversion rate of organic acids in the dry anaerobic digestion.

DETAILED DESCRIPTION OF THE EMBODIMENTS

Figure 1:
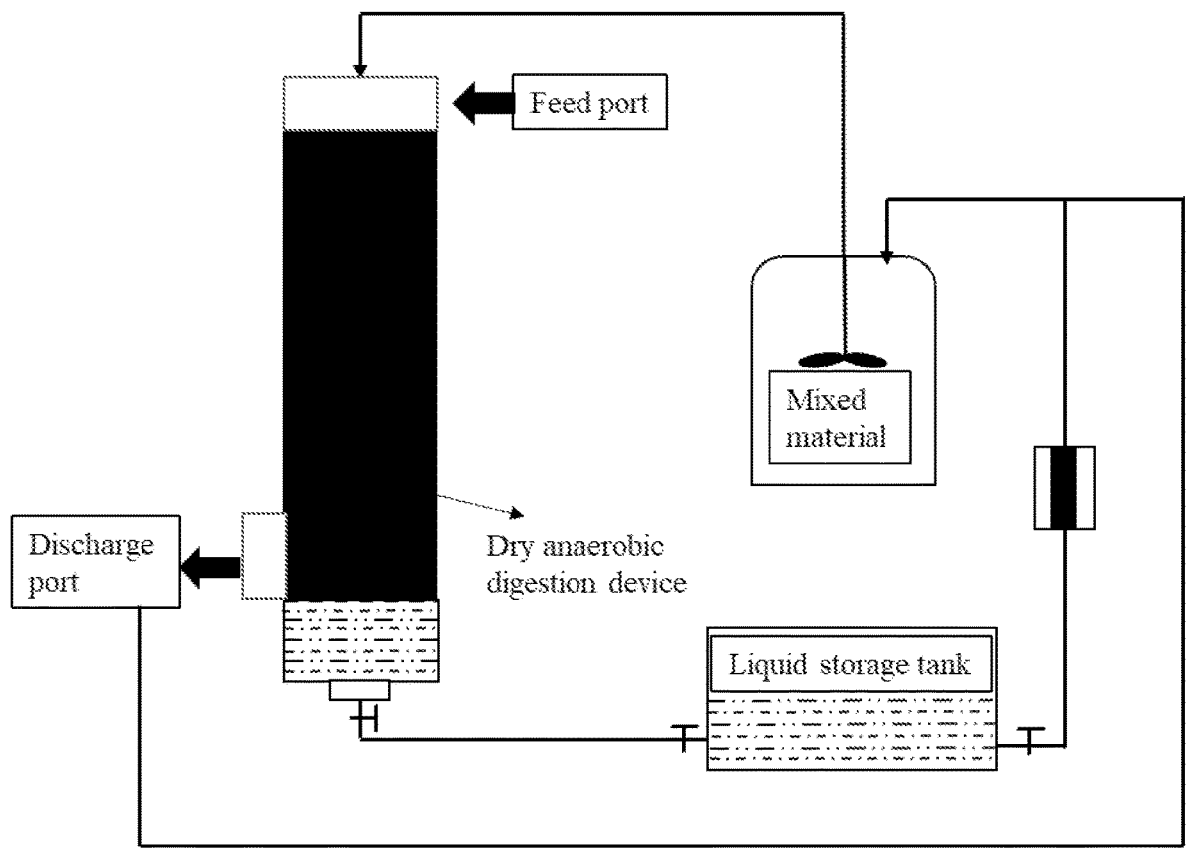
FIG. 1 shows a device flow chart in Example 1 of the present disclosure.

The present disclosure provides a method for two-phase partitioning production of an MCFA by dry anaerobic digestion, including the following steps:

1) mixing straw, livestock and poultry manure, and a composite microbial inoculant to obtain a fermentation material; where the composite microbial inoculant includes *Lactobacillus plantarum* and *Clostridium*;
2) inoculating sludge at a bottom of a dry anaerobic digestion device, filling an upper part of the sludge with the fermentation material, and conducting first dry anaerobic digestion for 3 d to 7 d; where the sludge is acclimated by an acid;
3) conducting second dry anaerobic digestion by means of continuous feeding and discharging after the first dry anaerobic digestion is completed; where a material residence time and a material feeding-discharging frequency of the second dry anaerobic digestion are determined according to an average pH value and an average redox potential of a resulting intermediate material in a top ¼ to ⅓ area of the dry anaerobic digestion device after the first dry anaerobic digestion is completed;

when the intermediate material has an average pH value of less than 5.5 and an average redox potential of less than −350 mV, the second dry anaerobic digestion is conducted with a material residence time of 7 d to 15 d and a material feeding-discharging frequency of 48 h/time to 72 h/time;

when the intermediate material has an average pH of 5.5 to 6.5 and/or an average redox potential of −350 mV to −150 mV, the second dry anaerobic digestion is conducted with a material residence time of 5 d to 7 d and a material feeding-discharging frequency of 12 h/time to 24 h/time; and when the intermediate material has an average pH value of more than 6.5 and an average redox potential of more than −150 mV, the second dry anaerobic digestion is conducted with a material residence time of 3 d to 5 d and a material feeding-discharging frequency of 6 h/time to 12 h/time; and 4) subjecting a fermentation product obtained in the second dry anaerobic digestion to solid-liquid separation, and collecting a liquid component having the MCFA.

In the present disclosure, straw, livestock and poultry manure, and a composite microbial inoculant are mixed to obtain a fermentation material; where the composite microbial inoculant includes *Lactobacillus plantarum* and *Clostridium* sp.

In the present disclosure, the straw preferably includes yellow corn silage straw; and the livestock and poultry manure preferably includes cow manure. The straw and the livestock and poultry manure are at a mass ratio of preferably 6:4 to 7:3, and this carbon-nitrogen ratio is more conducive to the growth and metabolism of microorganisms, promotes substrate conversion, and increases organic acid production; the straw and the livestock and poultry manure each have a solid content of greater than 25%; the composite microbial inoculant accounts for preferably 10% to 20%, more preferably 15% of a total mass of the straw and the livestock and poultry manure.

In the present disclosure, the *Lactobacillus plantarum* and the *Clostridium* independently have an effective viable count of preferably 0.1 billion cfu/g to 0.2 billion cfu/g; the *Lactobacillus plantarum* and the *Clostridium* are at an effective viable count ratio of preferably 1:1; the *Lactobacillus plantarum* and the *Clostridium* are preferably purchased from the China Center of Industrial Culture Collection (CICC); the *Lactobacillus plantarum* and the *Clostridium* are used to produce lactic acid and volatile fatty acids; the *Lactobacillus plantarum* has a deposit number of preferably CICC 21790; and the *Clostridium* has a deposit number of preferably CICC 24702.

In the present disclosure, acetic acid and lactic acid are produced directionally by coupling and adjusting the ratio of raw materials and adding a high-efficiency decomposing microbial inoculant, and serve as electron acceptors and electron donors, respectively, without additional electron donors. Compared with the preparation of MCFAs by traditional chemical methods, the method of the present disclosure reduces a preparation cost.

In the present disclosure, sludge is inoculated at a bottom of a dry anaerobic digestion device, an upper part of the sludge is filled with the fermentation material, and first dry anaerobic digestion is conducted for 3 d to 7 d; where the sludge is acclimated by an acid. The first dry anaerobic digestion is a pre-acidification process.

In the present disclosure, the fermentation material can be filled up to an effective volume of the dry anaerobic digestion device.

In the present disclosure, the sludge is preferably acclimated by lactic acid. A preparation process of the sludge acclimated by lactic acid preferably includes: adding the lactic acid with a concentration of 10 g/L into anaerobic sludge to allow fermentation in a fermenter; where the fermentation is conducted at 38° C. and a pH value of preferably 5.5 until caproic acid in a resulting fermentation system has a concentration of 3 g/L to 4 g/L. The sludge acclimated by lactic acid can shorten a fermentation time, and improve a conversion efficiency of organic waste, thereby increasing a degradation efficiency of raw materials and an output of organic acids.

In the present disclosure, the first dry anaerobic digestion is conducted at preferably 35° C. to 45° C., more preferably 40° C.

In the present disclosure, second dry anaerobic digestion is conducted by means of continuous feeding and discharging after the first dry anaerobic digestion is completed; where a material residence time and a material feeding-discharging frequency of the second dry anaerobic digestion are determined according to an average pH value and an average redox potential of a resulting intermediate material in a top ¼ to ⅓ area of the dry anaerobic digestion device after the first dry anaerobic digestion is completed; a ratio of different materials is determined according to the average pH value and the average redox potential of the resulting intermediate material in the upper ¼ to ⅓ area of the dry anaerobic digestion device after the first dry anaerobic digestion is completed;

when the intermediate material has an average pH value of less than 5.5 and an average redox potential of less than −350 mV, the second dry anaerobic digestion is conducted with a material residence time of 7 d to 15 d and a material feeding-discharging frequency of 48 h/time to 72 h/time;

when the intermediate material has an average pH of 5.5 to 6.5 and/or an average redox potential of −350 mV to −150 mV, the second dry anaerobic digestion is conducted with a material residence time of 5 d to 7 d and a material feeding-discharging frequency of 12 h/time to 24 h/time; and when the intermediate material has an average pH value of more than 6.5 and an average redox potential of more than −150 mV, the second dry anaerobic digestion is conducted with a material residence time of 3 d to 5 d and a material feeding-discharging frequency of 6 h/time to 12 h/time.

In the present disclosure, the lower ¼ to ⅓ area of the dry anaerobic digestion device during the second dry anaerobic digestion has a pH value of preferably 5.5 to 6.5, more preferably 5.8 to 6.

In the present disclosure, when a liquid produced in the upper ¼ to ⅓ area of the dry anaerobic digestion device flows to the lower ¼ to ⅓ area at a liquid decline rate of not more than 1.0 g/L to 1.5 g/L or the lower ¼ to ⅓ area of the dry anaerobic digestion device has a material porosity of not more than 25% to 30%, the material residence time is reduced to 9 d.

In the present disclosure, the lower ¼ to ⅓ area of the dry anaerobic digestion device automatically adjusts the pH value to 5.5 to 6.5. By adjusting the ratio of materials and the material residence time, after the hydrolytic acidification in the upper ¼ to ⅓ area of the dry anaerobic digestion device is completed, materials rich in acetic acid and lactic acid are transported to the lower ¼ to ⅓ area of the dry anaerobic digestion device along with sinking of the incoming and outgoing materials and the flow of the materials themselves, such that the lower ¼ to ⅓ area has an ambient pH that is always maintained at 5.5 to 6.5. Moreover, these conditions facilitate the progress of carbon chain extension.

The material residence time refers to an average residence time of materials to be treated in a reactor, and the material residence time is a ratio of a volume of the dry anaerobic digestion device to an amount of the added materials. A material residence time of 9 d to 15 d and an SCFA residence time of 3 d to 7 d are controlled by adjusting the amount of incoming and outgoing materials, so as to maintain an acid production rate at 3 g/L·d to 4 g/L·d and a liquid decline rate at 0.24 L/d to 0.31 L/d in the system. The liquid decline rate is calculated based on a leachate collection volume per day and a volume of the dry anaerobic digestion device. The leachate collection volume is 0.05 L/L d to 0.08 L/L d and a material porosity is 30% to 40%, and a transition system is constructed with an upper area to produce the acetic acid and lactic acid by hydrolytic acidification and coupled with a lower area to synthesize the MCFA. In this way, a two-phase partitioning production process of MCFA by integrated dry anaerobic digestion is constructed.

In the present disclosure, a fermentation product obtained in the second dry anaerobic digestion is subjected to solid-liquid separation, and a liquid component having the MCFA is collected.

In the present disclosure, the solid-liquid separation preferably includes: collecting the fermentation product to a bottom of the dry anaerobic digestion device through a perforated partition in the dry anaerobic digestion device.

In the present disclosure, the method preferably further includes the following step after the liquid component having the MCFA is collected: extracting the MCFA in the liquid component.

In the present disclosure, the method preferably further includes the following step after the MCFA in the liquid component is extracted: refluxing a residual liquid obtained by the extraction to the dry anaerobic digestion device when lactic acid and acetic acid in the dry anaerobic digestion device have a total concentration of not more than 8 g/L to 10 g/L. The residual liquid obtained by the extraction has a reflux volume accounting for preferably 10% to 20%, more preferably 15% of a feed amount by mass. The residual liquid obtained by the extraction is preferably refluxed to the dry anaerobic digestion device by spraying, at a spraying frequency of preferably 4 times/day to 6 times/day and a spraying volume of preferably 1 L/time to 2 L/time.

In the present disclosure, after the solid-liquid separation is completed, a solid component is further preferably collected. The solid component contains abundant carbon chain extension bacteria, a part of which can be reused as the sludge at a concentration of preferably 10% to 20% of a mass of the materials; and the remaining part can be used to prepare an organic fertilizer.

The technical solutions of the present disclosure will be clearly and completely described below with reference to the examples of the present disclosure.

Example 1

Figure 2:
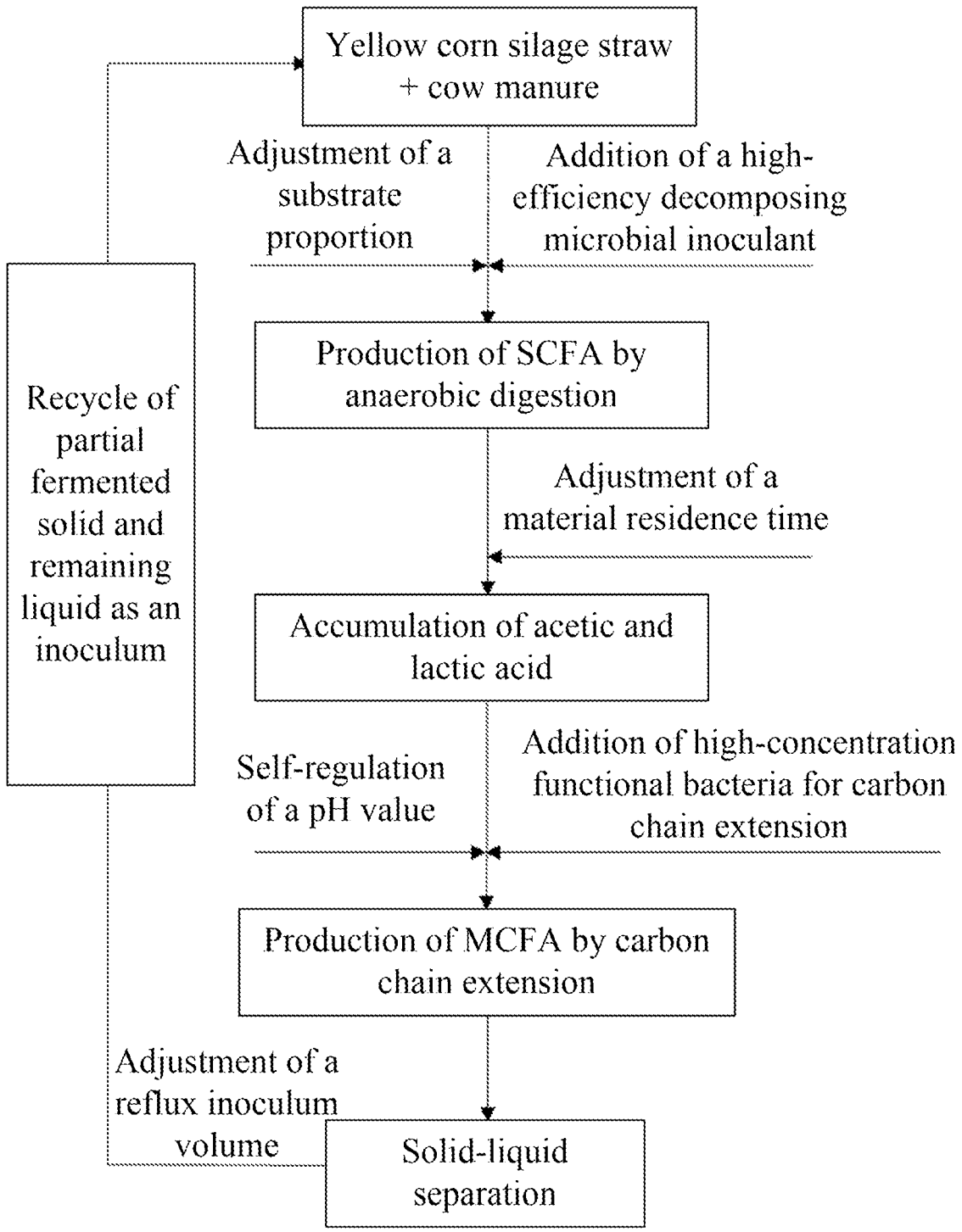
FIG. 2 shows a process flow chart in Example 1 of the present disclosure.

A device flow chart and a process flow chart of Example 1 were shown in FIG. 1 and FIG. 2 respectively.
(1) Corn straw and cow manure as fermentation raw materials were mixed under a total TS of 30% at a mass ratio of 7:3 to obtain a mixture, and the mixture was mixed with a high-efficiency decomposing microbial inoculant in a mass ratio of 1:10, fully stirred and then added into a 10 L anaerobic digestion device to allow anaerobic digestion; where
the high-efficiency decomposing microbial inoculant was a composite microbial inoculant composed of *Lactobacillus plantarum* and *Clostridium* and purchased from the CICC, and the *Lactobacillus plantarum* and the *Clostridium* independently had an effective viable count of 0.2 billion cfu/g; the *Lactobacillus plantarum* had a deposit number of CICC 21790; and the *Clostridium* had a deposit number of CICC 24702; and
before the anaerobic digestion was started, sludge with a carbon chain extension function was inoculated to a bottom of the anaerobic digestion device at an addition amount of 1/3 of an effective volume of the anaerobic digestion device (a sum of the amount of materials added and an inoculum volume of the substrate sludge was the effective volume of the anaerobic digestion device). Pre-acidification was conducted at a fermentation temperature of 38° C. for 3 d, such that lactic acid and acetic acid in an obtained fermentation system each had a concentration of 14.4 g/L, a pH value of the fermentation environment was 5.5, and the acidic environment could be maintained until the 9th day.

A preparation process of the sludge with a carbon chain extension function included: the lactic acid with a concentration of 10 g/L was added to the anaerobic sludge and then fermented at 38° C. in a fermenter until a concentration of caproic acid in the fermentation system reached (3-4) g/L.
(2) After the pre-acidification was conducted for 3 d, a feeding and discharging method was changed to continuous feeding and discharging every day, where a material residence time was 11 d, an acid production rate was 3.7 g/L·d, a material porosity was 30% and was stable above 30% after 11 d of anaerobic digestion, and a leachate collection volume was 1.5 L/L d. After 20 d of continuous anaerobic digestion, the leachate collection volume was not more than 0.5 L/L d, and the material residence time was adjusted to 9 d. After 15 d of anaerobic digestion, the concentration of caproic acid in the output was 5.4 g/L·d.
(3) An obtained fermentation product was subjected to solid-liquid separation, and a part of a fermented solid obtained in the output was used as an inoculum, while the remaining part was used to prepare organic fertilizers; after a liquid phase was collected in a liquid storage tank and extracted to obtain the MCFA, the remaining liquid was used as an inoculum and sprayed back to a mixing device.

Comparative Example 1

This comparative example provided a method similar to that of Example 1, and differed in that: the fermentation raw materials in step (1) included corn straw and pig manure.

Comparative Example 2

This comparative example provided a method similar to that of Example 1, and differed in that: the fermentation raw materials in step (1) included corn straw and chicken manure.

Comparative Example 3

This comparative example provided a method similar to that of Example 1, and differed in that: the straw and the cow manure in step (1) were at a mass ratio of 6:4.

Comparative Example 4

This comparative example provided a method similar to that of Example 1, and differed in that: the straw and the cow manure in step (1) were at a mass ratio of 5:5.

Comparative Example 5

This comparative example provided a method similar to that of Example 1, and differed in that: the material residence time in step (2) was 5 d.

Comparative Example 6

This comparative example provided a method similar to that of Example 1, and differed in that: the material residence time in step (2) was 7 d.

Comparative Example 7

This comparative example provided a method similar to that of Example 1, and differed in that: the material residence time in step (2) was 15 d.

The concentrations of lactic acid, acetic acid, and caproic acid, as well as the acid production rate and material porosity of the fermentation products of Example 1 and Comparative Examples 1 to 7 were measured. The contents of the organic acids were determined by gas chromatography, and sample preparation and detection methods referred to the literature [YU Jiadong, ZHAO Lixin, FENG Jing, et al. Research on the influencing factors of mixed dry anaerobic digestion of straw and cow manure in batch type [J]. *Transactions of the Chinese Society of Agricultural Engineering,* 2018, 34(15): 215-221.]. The material porosity was measured according to a detection method of basic soil properties, referring to [SHEN Qirong. General Introduction to Soil and Fertilizer Science [M]. Beijing: Higher Education Press, 2001]. The results were shown in Table 1.

TABLE 1

Concentrations of lactic acid, acetic acid, and caproic acid, as well as acid production rate and material porosity in different groups

| Group | Lactic acid (g/L · d) | Acetic acid (g/L · d) | Caproic acid (g/L · d) | Acid production rate (g/L · d) | Material porosity (%) |
|---|---|---|---|---|---|
| Example 1 | 8.40 | 6.0 | 5.4 | 3.70 | 30 |
| Comparative Example 1 | 6.64 | 4.60 | 4.1 | 2.77 | 33 |
| Comparative Example 2 | 7.29 | 3.80 | 3.6 | 2.68 | 32 |
| Comparative Example 3 | 6.90 | 5.10 | 4.2 | 2.97 | 25 |
| Comparative Example 4 | 6.81 | 4.73 | 3.8 | 2.80 | 24 |
| Comparative Example 5 | 7.54 | 5.08 | 2.9 | 3.00 | 27 |
| Comparative Example 6 | 7.31 | 5.22 | 3.1 | 3.20 | 30 |
| Comparative Example 7 | 6.82 | 4.10 | 2.8 | 2.65 | 40 |

As shown in Table 1, the concentrations of lactic acid, acetic acid, and caproic acid, as well as the acid production rate and the material porosity in the anaerobic digestion were measured; compared with the pig manure and chicken manure (Comparative Examples 1 to 2), the acid production rate of Example 1 was increased by 33.5700 and 38.0600, respectively, up to 3.70 g/L·d. Along with an increase of the proportion of cow manure in the substrate, the material porosity was reduced by 18% on average than that in Example 1; the concentrations of lactic acid, acetic acid, and caproic acid, and the acid production rate all showed a downward trend; a ratio of straw to cow manure at 7:3 was more conducive to the growth and metabolism of hydrolytic acid-producing microorganisms, and the concentrations of lactic acid and acetic acid each were as high as 14.4 g/L·d. Increasing the material residence time (Comparative Example 7) enhanced the material porosity, but the acid production rate dropped to 2.65 g/L-d; while shortening the material residence time resulted in insignificant differences in the material porosity.

It could be seen that in the present disclosure, the co-fermentation was conducted by mixing straw and cow manure as a substrate, a proportion of straw in the substrate was increased, the material residence time was appropriately increased, and the material porosity was maintained at about 3000. These factors helped to increase the material conversion rate and acid production rate.

Although the above example has described the present disclosure in detail, they are only a part of, not all of, the examples of the present disclosure. Other examples may also be obtained by persons based on the examples without creative efforts, and all of these examples shall fall within the protection scope of the present disclosure.

What is claimed is:

1. A method for two-phase partitioning production of a medium-chain fatty acid (MCFA) by dry anaerobic digestion, comprising the following steps:
   1) Mixing straw, livestock and poultry manure, and a composite microbial inoculant to obtain a fermentation material; wherein the composite microbial inoculant comprises *Lactobacillus plantarum* and *Clostridium*; and the livestock and poultry manure comprises cow manure; wherein the straw and the livestock and poultry manure are at a mass ratio of 6:4 to 7:3; and the composite microbial inoculant accounts for 10% to 20% of a total mass of the straw and the livestock and poultry manure;
   2) Inoculating sludge at a bottom of a dry anaerobic digestion device, filling an upper part of the sludge with the fermentation material, and conducting first dry anaerobic digestion for 3 d to 7 d; wherein the sludge is acclimated by an acid;
   3) Conducting second dry anaerobic digestion by means of continuous feeding and discharging after the first dry anaerobic digestion is completed; wherein
   a material residence time and a material feeding-discharging frequency of the second dry anaerobic digestion are determined according to an average pH value and an average redox potential of a resulting intermediate material in a top ¼ to ⅓ area of the dry anaerobic digestion device after the first dry anaerobic digestion is completed;
   when the intermediate material has an average pH value of less than 5.5 and an average redox potential of less than −350 mV, the second dry anaerobic digestion is conducted with a material residence time of 7 d to 15 d and a material feeding-discharging frequency of 48 h/time to 72 h/time;
   when the intermediate material has an average pH of 5.5 to 6.5 and/or an average redox potential of −350 mV to −150 mV, the second dry anaerobic digestion is conducted with a material residence time of 5 d to 7 d and a material feeding-discharging frequency of 12 h/time to 24 h/time; and
   when the intermediate material has an average pH value of more than 6.5 and an average redox potential of more than −150 mV, the second dry anaerobic digestion is conducted with a material residence time of 3 d to 5 d and a material feeding-discharging frequency of 6 h/time to 12 h/time; and
   4) Subjecting a fermentation product obtained in the second dry anaerobic digestion to solid-liquid separation, and collecting a liquid component having the MCFA.

2. The method according to claim 1, wherein the straw comprises yellow corn silage straw.

3. The method according to claim 1, wherein the *Lactobacillus plantarum* and the *Clostridium* independently have an effective viable count of 0.1 billion cfu/g to 0.2 billion cfu/g; and the *Lactobacillus plantarum* and the *Clostridium* are at an effective viable count ratio of 1:1.

4. The method according to claim 1, wherein the first dry anaerobic digestion and the second dry anaerobic digestion independently are conducted at 35° C. to 45° C.

5. The method according to claim 1, wherein a bottom ¼ to ⅓ area of the dry anaerobic digestion device has a pH value of 5.5 to 6.5 during the second dry anaerobic digestion.

6. The method according to claim 1, wherein when a liquid produced in the upper ¼ to ⅓ area of the dry anaerobic digestion device flows to the lower ¼ to ⅓ area at a liquid decline rate of not more than 1.0 g/L to 1.5 g/L or the lower ¼ to ⅓ area of the dry anaerobic digestion device has a material porosity of not more than 25% to 30%, the material residence time is reduced to 9 d.

7. The method according to claim 1, further comprising the following step after the liquid component having the MCFA is collected: extracting the MCFA in the liquid component.

8. The method according to claim 7, further comprising the following step after the MCFA in the liquid component is extracted: refluxing a residual liquid obtained by the extraction to the dry anaerobic digestion device when lactic acid and acetic acid in the dry anaerobic digestion device have a total concentration of not more than 8 g/L to 10 g/L.

9. The method according to claim 8, wherein the residual liquid obtained by the extraction has a reflux volume accounting for 10% to 20% of a feed amount by mass.

* * * * *